(12) United States Patent
Girouard et al.

(10) Patent No.: US 7,127,290 B2
(45) Date of Patent: Oct. 24, 2006

(54) CARDIAC RHYTHM MANAGEMENT SYSTEMS AND METHODS PREDICTING CONGESTIVE HEART FAILURE STATUS

(75) Inventors: Steven D. Girouard, Woodbury, MN (US); Jeffrey E. Stahmann, Ramsey, MN (US); Robert J. Sweeney, Woodbury, MN (US); Bruce H. KenKnight, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 610 days.

(21) Appl. No.: 10/213,268

(22) Filed: Aug. 6, 2002

(65) Prior Publication Data

US 2003/0055461 A1 Mar. 20, 2003

Related U.S. Application Data

(63) Continuation-in-part of application No. 09/850,537, filed on May 7, 2001, now Pat. No. 7,050,846, which is a continuation of application No. 09/411,345, filed on Oct. 1, 1999, now Pat. No. 6,272,377.

(51) Int. Cl.
*A61N 1/365* (2006.01)
(52) U.S. Cl. .................................. 607/17; 600/515
(58) Field of Classification Search ............... 600/515; 607/17
See application file for complete search history.

(56) References Cited

U.S. PATENT DOCUMENTS

| | | | | |
|---|---|---|---|---|
| 4,129,125 A * | 12/1978 | Lester et al. ............. | 600/484 |
| 4,422,459 A | 12/1983 | Simson ..................... | 128/702 |
| 4,458,691 A | 7/1984 | Netravali .................. | 128/705 |
| 4,458,692 A | 7/1984 | Simson ..................... | 128/705 |
| 4,492,235 A | 1/1985 | Sitrick ..................... | 128/705 |
| 4,519,395 A | 5/1985 | Hrushesky ................ | 128/671 |
| 4,680,708 A | 7/1987 | Ambos et al. ............. | 364/417 |
| 4,732,157 A | 3/1988 | Kaplan et al. ............ | 128/696 |
| 4,754,753 A | 7/1988 | King ........................ | 128/699 |
| 4,777,960 A | 10/1988 | Berger et al. ............. | 128/706 |
| 4,905,706 A | 3/1990 | Duff et al. ................ | 128/701 |
| 4,924,875 A | 5/1990 | Chamoun .................. | 128/696 |
| 4,930,075 A | 5/1990 | Kortas ..................... | 364/413.06 |
| 4,957,115 A * | 9/1990 | Selker ...................... | 600/509 |
| 4,960,129 A | 10/1990 | dePaola et al. ........... | 128/695 |
| 5,003,976 A * | 4/1991 | Alt .......................... | 607/18 |
| 5,014,698 A | 5/1991 | Cohen ...................... | 128/419 |
| 5,020,540 A | 6/1991 | Chamoun .................. | 128/696 |
| 5,042,497 A | 8/1991 | Shapland .................. | 128/696 |
| 5,092,341 A | 3/1992 | Kelen ....................... | 128/702 |

(Continued)

FOREIGN PATENT DOCUMENTS

EP   0547733   6/1993

(Continued)

OTHER PUBLICATIONS

Carlson, Gerrard.M. ,et al. ,"Cardiac Rhythm Management System Using Time-Domain Heart Rate Variability Indicia",U.S. Appl. No. 09/802,316, (Mar. 8, 2001), 34.

(Continued)

*Primary Examiner*—Angela D. Sykes
*Assistant Examiner*—Lenwood Faulcon, Jr.
(74) *Attorney, Agent, or Firm*—Schwegman, Lundberg, Woessner & Kluth, P.A.

(57) ABSTRACT

This document describes, among other things, systems, devices, and methods for predicting how the status of the patient's congestive heart failure (CHF) condition will progress in the future. In one example, a therapy is provided or adjusted at least in part in response to the prediction.

55 Claims, 2 Drawing Sheets

U.S. PATENT DOCUMENTS

| | | | |
|---|---|---|---|
| 5,109,862 A | 5/1992 | Kelen et al. | 128/702 |
| 5,113,869 A | 5/1992 | Nappholz et al. | 128/696 |
| 5,129,394 A | 7/1992 | Mehra | |
| 5,148,812 A | 9/1992 | Verrier et al. | 128/704 |
| 5,161,539 A | 11/1992 | Evans et al. | 128/696 |
| 5,181,519 A | 1/1993 | Bible | 128/704 |
| 5,188,116 A | 2/1993 | Pommrehn et al. | 128/696 |
| 5,199,428 A | 4/1993 | Obel et al. | 128/419 C |
| 5,203,326 A | 4/1993 | Collins | 128/419 PG |
| 5,215,099 A | 6/1993 | Haberl et al. | 128/702 |
| 5,217,021 A | 6/1993 | Steinhaus et al. | 128/702 |
| 5,265,617 A | 11/1993 | Verrier et al. | 128/704 |
| 5,277,189 A | 1/1994 | Jacobs | 128/696 |
| 5,285,793 A | 2/1994 | Slovut et al. | 128/706 |
| 5,318,037 A | 6/1994 | Evans et al. | 128/696 |
| 5,318,592 A | 6/1994 | Schaldach | 607/5 |
| 5,330,505 A | 7/1994 | Cohen | 607/6 |
| 5,330,507 A | 7/1994 | Schwartz | 607/14 |
| 5,377,687 A | 1/1995 | Evans et al. | 128/700 |
| 5,411,531 A | 5/1995 | Hill et al. | 607/14 |
| 5,417,717 A * | 5/1995 | Salo et al. | 607/18 |
| 5,419,338 A | 5/1995 | Sarma et al. | 128/703 |
| 5,431,689 A | 7/1995 | Weinberg et al. | 607/14 |
| 5,437,285 A | 8/1995 | Verrier et al. | 128/702 |
| 5,507,784 A | 4/1996 | Hill et al. | 607/14 |
| 5,509,425 A | 4/1996 | Feng | 128/702 |
| 5,509,925 A | 4/1996 | Adams et al. | 607/5 |
| 5,534,015 A | 7/1996 | Kroll et al. | 607/7 |
| 5,555,888 A | 9/1996 | Brewer et al. | 128/702 |
| 5,555,889 A | 9/1996 | Karagueuzian et al. | 128/705 |
| 5,558,638 A | 9/1996 | Evers et al. | |
| 5,560,367 A | 10/1996 | Haardt et al. | 128/702 |
| 5,560,368 A | 10/1996 | Berger | 128/703 |
| 5,560,370 A | 10/1996 | Verrier et al. | 128/705 |
| 5,562,711 A * | 10/1996 | Yerich et al. | 607/17 |
| 5,570,696 A | 11/1996 | Arnold et al. | 128/707 |
| 5,578,061 A | 11/1996 | Stroetmann et al. | 607/4 |
| 5,609,158 A | 3/1997 | Chan | 128/705 |
| 5,645,069 A | 7/1997 | Lee | 128/702 |
| 5,655,540 A | 8/1997 | Seegobin | 128/702 |
| 5,658,318 A | 8/1997 | Stroetmann et al. | 607/6 |
| 5,678,561 A | 10/1997 | Karagueuzian et al. | 178/705 |
| 5,682,901 A | 11/1997 | Kamen | 128/706 |
| 5,713,367 A | 2/1998 | Arnold et al. | 128/704 |
| 5,713,938 A | 2/1998 | Chiang et al. | |
| 5,724,983 A * | 3/1998 | Selker et al. | 600/301 |
| 5,730,142 A | 3/1998 | Sun et al. | 128/705 |
| 5,743,267 A | 4/1998 | Nikolic et al. | |
| 5,749,900 A | 5/1998 | Schroeppel et al. | 607/4 |
| 5,758,652 A | 6/1998 | Nikolic | |
| 5,772,604 A | 6/1998 | Langberg et al. | 600/518 |
| 5,778,881 A | 7/1998 | Sun et al. | 128/696 |
| 5,782,888 A | 7/1998 | Sun et al. | 607/27 |
| 5,785,702 A | 7/1998 | Murphy-Chutorian et al. | 606/7 |
| 5,788,643 A | 8/1998 | Feldman | |
| 5,792,197 A * | 8/1998 | Nappholz | 607/17 |
| 5,819,007 A | 10/1998 | Elghazzawi | 395/51 |
| 5,836,987 A | 11/1998 | Baumann et al. | |
| 5,868,680 A | 2/1999 | Steiner et al. | 600/518 |
| 5,871,505 A | 2/1999 | Adams et al. | 607/5 |
| 5,876,353 A | 3/1999 | Riff | |
| 5,891,176 A | 4/1999 | Bornzin | |
| 5,931,834 A | 8/1999 | Murphy-Chutorian et al. | 606/7 |
| 5,935,081 A | 8/1999 | Kadhiresan | |
| 5,957,861 A | 9/1999 | Combs et al. | |
| 5,974,340 A | 10/1999 | Kadhiresan | |
| 5,976,082 A | 11/1999 | Wong et al. | 600/300 |
| 6,021,351 A | 2/2000 | Kadhiresan et al. | |
| 6,022,315 A | 2/2000 | Iliff | 600/300 |
| 6,035,233 A * | 3/2000 | Schroeppel et al. | 600/515 |
| 6,045,513 A | 4/2000 | Stone et al. | |
| 6,064,906 A | 5/2000 | Langberg et al. | 600/518 |
| 6,067,466 A | 5/2000 | Selker et al. | 600/513 |
| 6,102,874 A | 8/2000 | Stone et al. | |
| 6,104,949 A | 8/2000 | Pitts Crick et al. | |
| 6,110,109 A | 8/2000 | Hu et al. | 600/300 |
| 6,112,116 A | 8/2000 | Fischell et al. | 600/517 |
| 6,115,627 A | 9/2000 | Street | 600/515 |
| 6,128,526 A | 10/2000 | Stadler et al. | 600/517 |
| 6,129,744 A | 10/2000 | Boute | |
| 6,135,970 A | 10/2000 | Kadhiresan et al. | |
| 6,148,228 A | 11/2000 | Fang et al. | 600/509 |
| 6,155,267 A | 12/2000 | Nelson | 128/899 |
| 6,190,324 B1 | 2/2001 | Kieval et al. | |
| 6,223,082 B1 | 4/2001 | Bakels et al. | |
| 6,246,910 B1 | 6/2001 | Bonnet et al. | |
| 6,272,377 B1 | 8/2001 | Sweeney et al. | 600/515 |
| 6,275,727 B1 | 8/2001 | Hopper et al. | |
| 6,277,078 B1 | 8/2001 | Porat et al. | |
| 6,314,323 B1 | 11/2001 | Ekwall | |
| 6,328,699 B1 | 12/2001 | Eigler et al. | |
| 6,360,123 B1 | 3/2002 | Kimchi et al. | |
| 6,371,922 B1 | 4/2002 | Baumann et al. | |
| 6,400,982 B1 | 6/2002 | Sweeney et al. | 600/515 |
| 6,409,675 B1 | 6/2002 | Turcott | |
| 6,438,408 B1 | 8/2002 | Mulligan et al. | |
| 6,449,509 B1 | 9/2002 | Park et al. | |
| 6,454,707 B1 | 9/2002 | Casscells, III et al. | |
| 6,454,719 B1 | 9/2002 | Greenhut | |
| 6,456,880 B1 | 9/2002 | Park et al. | |
| 6,459,929 B1 | 10/2002 | Hopper et al. | |
| 6,459,934 B1 | 10/2002 | Kadhiresan | |
| 6,471,645 B1 | 10/2002 | Warkentin | |
| 6,473,640 B1 | 10/2002 | Erlebacher | |
| 6,473,646 B1 | 10/2002 | Sun et al. | |
| 6,473,647 B1 | 10/2002 | Bradley | |
| 6,480,733 B1 | 11/2002 | Turcott | |
| 6,491,639 B1 | 12/2002 | Turcott | |
| 6,497,655 B1 | 12/2002 | Linberg et al. | |
| 6,512,949 B1 | 1/2003 | Combs et al. | |
| 6,529,771 B1 | 3/2003 | Kieval et al. | |
| 6,539,249 B1 | 3/2003 | Kadhiresan et al. | |
| 6,561,984 B1 | 5/2003 | Turcott | |
| 6,572,557 B1 | 6/2003 | Tchou et al. | |
| 6,575,912 B1 | 6/2003 | Turcott | |
| 6,580,946 B1 | 6/2003 | Struble | |
| 6,589,188 B1 | 7/2003 | Street et al. | |
| 6,595,927 B1 | 7/2003 | Pitts-Crick et al. | |
| 6,600,949 B1 | 7/2003 | Turcott | |
| 6,641,542 B1 | 11/2003 | Cho et al. | |
| 6,643,548 B1 | 11/2003 | Mai et al. | |
| 6,645,153 B1 | 11/2003 | Kroll et al. | |
| 6,669,631 B1 | 12/2003 | Norris et al. | |
| 6,741,885 B1 | 5/2004 | Park et al. | |
| 6,752,765 B1 | 6/2004 | Jensen et al. | |
| 6,773,404 B1 | 8/2004 | Poezevera et al. | |
| 2001/0037067 A1 | 11/2001 | Tchou et al. | |
| 2001/0037069 A1 | 11/2001 | Carlson et al. | |
| 2002/0002389 A1 | 1/2002 | Bradley et al. | |
| 2002/0016550 A1 | 2/2002 | Sweeney et al. | |
| 2002/0062139 A1 | 5/2002 | Ding | |
| 2002/0091332 A1 | 7/2002 | Bombardini | |
| 2002/0099302 A1 | 7/2002 | Bardy et al. | |
| 2002/0123772 A1 | 9/2002 | Sun et al. | |
| 2002/0161412 A1 | 10/2002 | Sun et al. | |
| 2002/0169388 A1 | 11/2002 | Bowman et al. | |
| 2003/0004548 A1 | 1/2003 | Warkentin | |
| 2003/0009167 A1 | 1/2003 | Helland et al. | |
| 2003/0014084 A1 | 1/2003 | VanHout et al. | |
| 2003/0028221 A1 | 2/2003 | Zhu et al. | |
| 2003/0055344 A1 | 3/2003 | Eigler et al. | |
| 2003/0055345 A1 | 3/2003 | Eigler | |
| 2003/0074029 A1 | 4/2003 | Deno et al. | |
| 2003/0083702 A1 | 5/2003 | Stadler et al. | |

| | | | |
|---|---|---|---|
| 2003/0093125 A1 | 5/2003 | Zhu | |
| 2003/0100925 A1 | 5/2003 | Pape et al. | |
| 2003/0149453 A1 | 8/2003 | Kroll et al. | |
| 2003/0153953 A1 | 8/2003 | Park et al. | |
| 2003/0157493 A1 | 8/2003 | Sklar et al. | |
| 2003/0199933 A1 | 10/2003 | Struble et al. | |
| 2003/0199956 A1 | 10/2003 | Struble et al. | |
| 2003/0208240 A1 | 11/2003 | Pastore et al. | |
| 2003/0216657 A1 | 11/2003 | Holmstrom et al. | |
| 2003/0220580 A1 | 11/2003 | Alt | |
| 2004/0073093 A1 | 4/2004 | Hatlestad | |
| 2004/0102712 A1 | 5/2004 | Belalcazar et al. | |
| 2004/0116819 A1 | 6/2004 | Alt | |
| 2004/0172080 A1 | 9/2004 | Stadler et al. | |
| 2005/0080460 A1 | 4/2005 | Wang et al. | |

FOREIGN PATENT DOCUMENTS

| | | |
|---|---|---|
| EP | 1118307 | 7/2001 |
| EP | 1151719 | 11/2001 |
| EP | 1177764 | 2/2002 |
| EP | 1348463 | 10/2003 |
| EP | 1011802 | 6/2004 |
| WO | WO-9739792 | 10/1997 |
| WO | WO-0240096 | 5/2002 |
| WO | WO-03089033 | 10/2003 |
| WO | WO-2005028029 | 3/2005 |

OTHER PUBLICATIONS

Lincoln, William.C. ,et al. ,"Cardiac Rhytham Management System and Method Using Time Between Mitral Valve Closure and Aortic Ejection", U.S. Appl. No. 10/099,865,(Mar. 31, 2002),33.

Lincoln, William.C. ,et al. ,"Cardiac Rhythm Management System Selecting A-V Delay Based on Interval Between Atrial Depolarization and Mitral Valve Closure",U.S. Appl. No. 09/862,763, (May 21, 2001),26.

* cited by examiner

CARDIAC RHYTHM MANAGEMENT SYSTEMS AND METHODS PREDICTING CONGESTIVE HEART FAILURE STATUS

CROSS REFERENCE TO RELATED APPLICATION(S)

This patent application is a continuation-in-part of Sweeney et al. U.S. patent application Ser. No. 09/850,537, filed on May 7, 2001, now U.S. Pat. No. 7,050,846, entitled "CARDIAC RHYTHM MANAGEMENT SYSTEM WITH ARRHYTHMIA PREDICTION AND PREVENTION," which is, in turn, a continuation of Sweeney et al. U.S. patent application Ser. No. 09/411,345, filed on Oct. 1, 1999, and issued on Aug. 7, 2001 as U.S. Pat. No. 6,272,377, each of which is assigned to Cardiac Pacemakers, Inc., the specification of each which is incorporated herein by reference in its entirety.

TECHNICAL FIELD

This document relates generally to medical systems, devices, and methods, and particularly, but not by way of limitation, to cardiac rhythm management systems and methods predicting congestive heart failure status.

BACKGROUND

When functioning properly, the human heart maintains its own intrinsic rhythm. Its sinoatrial node generates intrinsic electrical cardiac signals that depolarize the atria, causing atrial heart contractions. Its atrioventricular node then passes the intrinsic cardiac signal to depolarize the ventricles, causing ventricular heart contractions. These intrinsic cardiac signals can be sensed on a surface electrocardiogram (ECG) obtained from electrodes placed on the patient's skin, or from electrodes implanted within the patient's body. The surface ECG waveform, for example, includes artifacts associated with atrial depolarizations ("P-waves") and those associated with ventricular depolarizations ("QRS complexes").

A normal heart is capable of pumping adequate blood throughout the body's circulatory system. However, some people have irregular cardiac rhythms, referred to as cardiac arrhythmias. Moreover, some patients have poor spatial coordination of heart contractions. In either case, diminished blood circulation may result. For such patients, a cardiac rhythm management system may be used to improve the rhythm and/or spatial coordination of heart contractions. Such systems are often implanted in the patient and deliver therapy to the heart.

One problem faced by physicians treating cardiovascular patients is the treatment of congestive heart failure (also referred to as "CHF"). Congestive heart failure, which can result from long-term hypertension, is a condition in which the muscle in the walls of at least one of the right and left sides of the heart deteriorates. By way of example, suppose the muscle in the walls of left side of the heart deteriorates. As a result, the left atrium and left ventricle become enlarged, and the heart muscle displays less contractility. This decreases cardiac output of blood through the circulatory system which, in turn, may result in an increased heart rate and less resting time between heartbeats. The heart consumes more energy and oxygen, and its condition typically worsens over a period of time.

In the above example, as the left side of the heart becomes enlarged, the intrinsic electrical heart signals that control heart rhythm may also be affected. Normally, such intrinsic signals originate in the sinoatrial (SA) node in the upper right atrium, traveling through electrical pathways in the atria and depolarizing the atrial heart tissue such that resulting contractions of the right and left atria are triggered. The intrinsic atrial heart signals are received by the atrioventricular (AV) node which, in turn, triggers a subsequent ventricular intrinsic heart signal that travels through specific electrical pathways in the ventricles and depolarizes the ventricular heart tissue such that resulting contractions of the right and left ventricles are triggered substantially simultaneously.

In the above example, where the left side of the heart has become enlarged due to congestive heart failure, however, the conduction system formed by the specific electrical pathways in the ventricle may be affected, as in the case of left bundle branch block (LBBB). As a result, ventricular intrinsic heart signals may travel through and depolarize the left side of the heart more slowly than in the right side of the heart. As a result, the left and right ventricles do not contract simultaneously, but rather, the left ventricle contracts after the right ventricle. This reduces the pumping efficiency of the heart. Moreover, in LBBB, for example, different regions within the left ventricle may not contract together in a coordinated fashion.

Cardiac rhythm management systems include, among other things, pacemakers, also referred to as pacers. Pacers deliver timed sequences of low energy electrical stimuli, called pace pulses, to the heart, such as via an intravascular lead wire or catheter (referred to as a "lead") having one or more electrodes disposed in or about the heart. Heart contractions are initiated in response to such pace pulses (this is referred to as "capturing" the heart). By properly timing the delivery of pace pulses, the heart can be induced to contract in proper rhythm, greatly improving its efficiency as a pump. Pacers are often used to treat patients with bradyarrhythmias, that is, hearts that beat too slowly, or irregularly. Such pacers may also coordinate atrial and ventricular contractions to improve pumping efficiency.

Cardiac rhythm management systems also include cardiac resynchronization therapy (CRT) devices for coordinating the spatial nature of heart depolarizations for improving pumping efficiency, such as for patients having CHF. For example, a CRT device may deliver appropriately timed pace pulses to different locations of the same heart chamber to better coordinate the contraction of that heart chamber or the CRT device may deliver appropriately timed pace pulses to different heart chambers to improve the manner in which these different heart chambers contract together.

Cardiac rhythm management systems also include defibrillators that are capable of delivering higher energy electrical stimuli to the heart. Such defibrillators include cardioverters, which synchronize the delivery of such stimuli to sensed intrinsic heart activity signals. Defibrillators are often used to treat patients with tachyarrhythmias, that is, hearts that beat too quickly. Such too-fast heart rhythms also cause diminished blood circulation because the heart isn't allowed sufficient time to fill with blood before contracting to expel the blood. Such pumping by the heart is inefficient. A defibrillator is capable of delivering a high energy electrical stimulus that is sometimes referred to as a defibrillation countershock, also referred to simply as a "shock." The countershock interrupts the tachyarrhythmia, allowing the heart to reestablish a normal rhythm for the efficient pumping of blood. In addition to pacers, CRT devices, and defibrillators, cardiac rhythm management systems also include devices that combine these functions, as well as monitors, drug delivery devices, and any other implantable or external systems or devices for diagnosing or treating the heart.

The present inventors have recognized that one problem presented by CHF patients is predicting how the status of the patient's CHF will progress in the future. The present inventors have recognized that there exists an unmet need for predicting future CHF status.

BRIEF DESCRIPTION OF THE DRAWINGS

In the drawings, which are offered by way of example, and not by way of limitation, and which are not necessarily drawn to scale, like numerals describe substantially similar components throughout the several views. Like numerals having different letter suffixes represent different instances of substantially similar components.

DETAILED DESCRIPTION

In the following detailed description, reference is made to the accompanying drawings, which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. Furthermore, all publications, patents, and patent documents referred to in this document are incorporated by reference herein in their entirety, as though individually incorporated by reference. In the event of inconsistent usages between this documents and those documents so incorporated by reference, the usage in the incorporated reference(s) should be considered supplementary to that of this document; for irreconcilable inconsistencies, the usage in this document controls.

This document discusses, among other things; systems, device., and methods that will be described in applications involving implantable medical devices including, but not limited to, implantable cardiac rhythm management systems such as pacemakers, cardioverter/defibrillators, pacer/defibrillators, biventricular or other multi-site resynchronization or coordination devices, and drug delivery systems. However, these systems, devices, and methods may be employed in unimplanted devices, including, but not limited to, external pacemakers, cardioverter/defibrillators, pacer/defibrillators, biventricular or other multi-site resynchronization or coordination devices, monitors, programmers and recorders, whether such devices are used for providing a diagnostic, a therapy, or both a diagnostic and a therapy.

Figure 1:
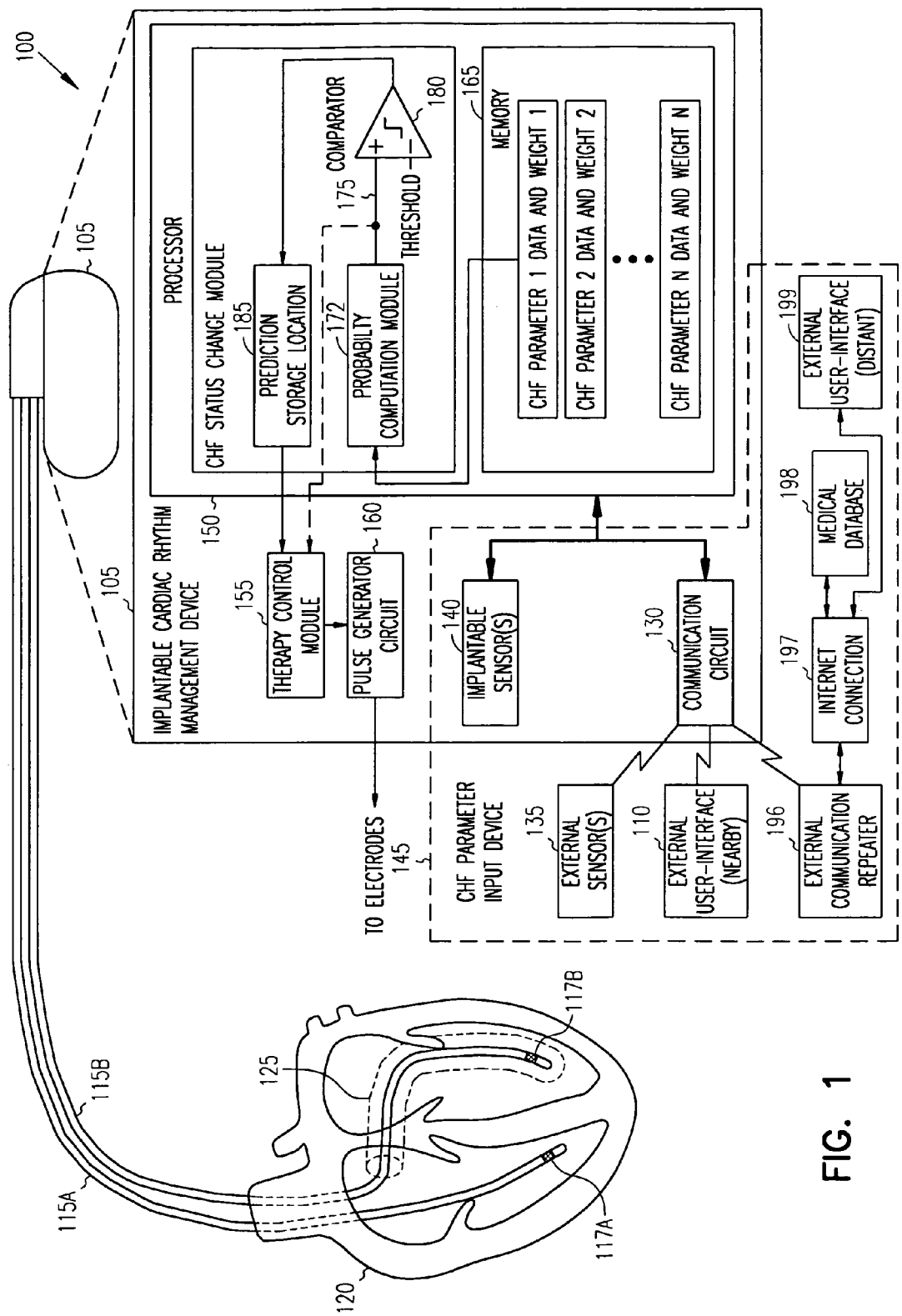
FIG. 1 is a schematic diagram illustrating generally, by way of example, but not by way of limitation, portions of a cardiac rhythm management system capable of predicting future congestive heart failure (CHF) status.

FIG. 1 is a schematic diagram illustrating generally, by way of example, but not by way of limitation, portions of a cardiac rhythm management system 100 capable of predicting future congestive heart failure (CHF) status. In this example, system 100 includes a hermetically sealed implantable cardiac rhythm management device 105 and a programmer or other external user interface 110. In this example, intracardiac leads 115A–B are catheters connected to device 105, with respective distal portions intravascularly introduced into heart 120. In the illustrative example of FIG. 1, a distal portion of lead 115A is introduced into a right ventricle of heart 120, and a distal portion of lead 115B is introduced through coronary sinus 125 (which, in this document, includes the great cardiac vein) into proximity with a wall of a left ventricle of heart 120. In this example, leads 115A–B each include one or more pacing and/or defibrillation electrodes, e.g., 117A–B, such as for providing pacing, resynchronization (e.g., for a CHF subject), cardioversion, and/or defibrillation therapy to heart 120.

In the example of FIG. 1, device 105 carries various electrical components, such as a communication circuit 130, which is capable of wirelessly communicating with a communication circuit of nearby remote external user interface 110. In another example, communication circuit 130 is capable of wirelessly communicating with a communication circuit of a distant remote external user interface 199, such as by using a nearby external communication repeater 196. In one example, repeater 196 is coupled to user interface 199 via internet connection 197. In another example, repeater 196 also communicatively couples device 105 to an electronic medical database 198, such as via internet connection 197. In a further example, communication circuit 130 of device 105 is communicatively coupled to a communication circuit of a weight scale or other external sensor 135. In one example, device 105 additionally or alternatively includes an implantable sensor 140 therewithin or implanted nearby and coupled thereto. For predicting a future change in a subject's CHF status, system 100 includes a CHF physiological parameter input device 145 and a processor 150 for performing the prediction by computing a weighted probability using at least two CHF physiological parameters obtained from CHF parameter input device 145, thereby increasing the accuracy of the future CHF status change prediction. CHF parameter input device 145 includes one or more of external sensor(s) 135, nearby external user interface 110, distant external user interface 199, computerized patient information medical database 198, and/or implantable sensor(s) 140. In one example, device 105 also includes a therapy control module 155, which uses an indication of the predicted probability of a CHF status change occurring within a predetermined future time period as at least one factor for adjusting a therapy provided by pulse generator circuit 160 through electrodes 117A–B to heart 120. In another example, device 105 communicates an indication of the predicted probability of a CHF status (or derived therefrom) to nearby external user interface 110 and/or more distant external user interface 199 to be provided to a physician, caregiver, patient, or other user.

In the example of FIG. 1, processor 150 is capable of sequencing through various control states such as, for example, by using a digital microprocessor having executable instructions stored in an associated instruction memory circuit, a microsequencer, or a state machine. However, processor 150 is capable of using many other hardware/firmware/software implementations. In the example of FIG.

1, processor 150 includes an on-board or off-board memory circuit 165, which is capable of storing data associated with at least two CHF physiologic parameters (e.g., CHF Parameter 1, CHF Parameter 2, . . . , CHF Parameter N) and corresponding conditional probabilities or other weights associated with each such parameter (e.g., Weight 1, Weight 2, . . . , Weight N). In general, each weight is computed using historical data relating the corresponding CHF physiologic parameter to CHF status. In one example, the historical data is obtained from the same subject from which the CHF physiologic information is obtained. In another example, the historical data is obtained from at least one different subject (for example, by accessing data in medical database 198). In a further example, the historical data is obtained from a population of subjects. Processor 150 also includes a CHF status change module 170, which may be implemented either in dedicated hardware or as a sequence of instructions executed by processor 150.

In another example, a weight is computed using not only its corresponding CHF physiologic parameter, but also using information about which other CHF physiologic parameter (and/or how many other CHF physiologic parameters) are also being used to predict the likelihood of a change in the subject's CHF status. In an illustrative example, suppose parameters A and B each have weights of 0.1, leading to a combined prediction weight of 0.2. In another example, however, parameters A and B each have weights of 0.1, when these parameters are individually used in the CHF status change prediction, but have a different (e.g., greater or lesser) weight when both are present (e.g., a stronger weight of 0.5 when both A and B are sufficiently present and used in the CHF status change prediction. Therefore, the weight values may depend on cross-correlation between two or more different CHF physiologic parameters. In one example, a matrix is used to store the weights, and the matrix index is used to access the particular weights that are appropriate for a particular combination of CHF physiologic parameters. In another example, the weight values depend on how many CHF physiologic parameters are being used to compute the likelihood of a subject's CHF status change. As an illustrative example, suppose CHF physiologic parameter A has a weight of 0.5 when it is used alone for predicting a subject's CHF status change. In another example, however, CHF physiologic parameter has a weight of 0.25 when used in combination with one other different CHF physiologic parameter (e.g., parameter B or parameter C, etc.).

In the example of FIG. 1, CHF status change module 170 includes a probability computation module 172 that computes a probability of the subject undergoing a change in CHF status using the weighted probability of the at least two CHF physiologic parameters. An indication of the computed probability is output at node 175 and input to comparator 180, which compares it to a predetermined threshold that is also input to comparator 180. The resulting comparison, which is stored at prediction storage location 185, provides a binary indication of whether the predicted change in CHF status is deemed significant. In one example, either this binary indication at node 190 of whether the predicted CHF status change is significant, or the underlying probability of a change in CHF status at 195 is provided to therapy control module 155, which responsively adjusts one or more therapy parameters controlling how pulse generator circuit 160 delivers therapy to heart 120. Either or both of the status indicators at 175 and/or 190 can also be communicated via nearby user interface 110 and/or more distant user interface 199.

Figure 2:
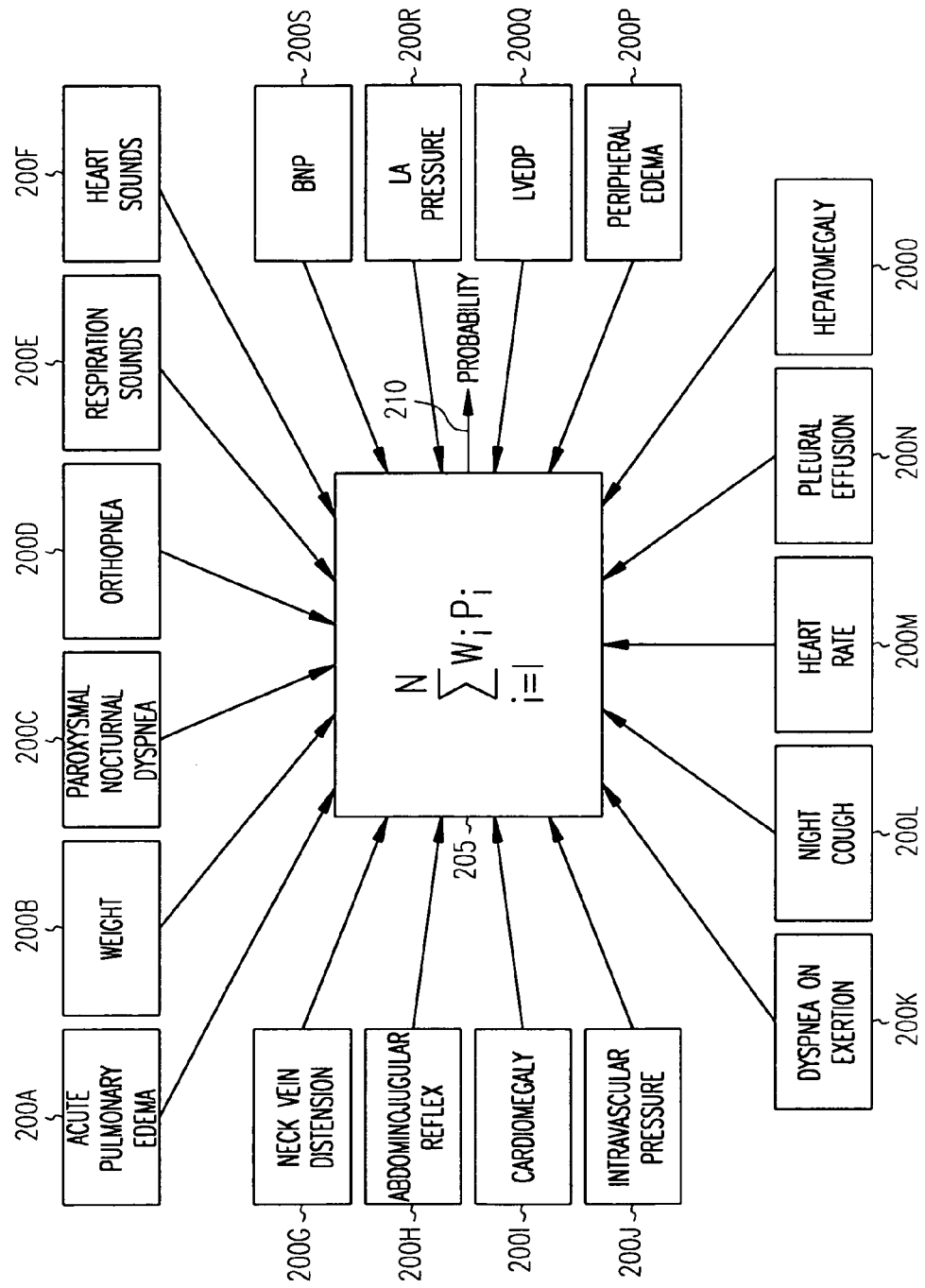
FIG. 2 is a graph illustrating generally, by way of example, but not by way of limitation, various CHF physiological parameters, at least two of which are used in the probability computation to provide a weighted probability of a CHF status change occurring during a predetermined future time period.
Figure 1:
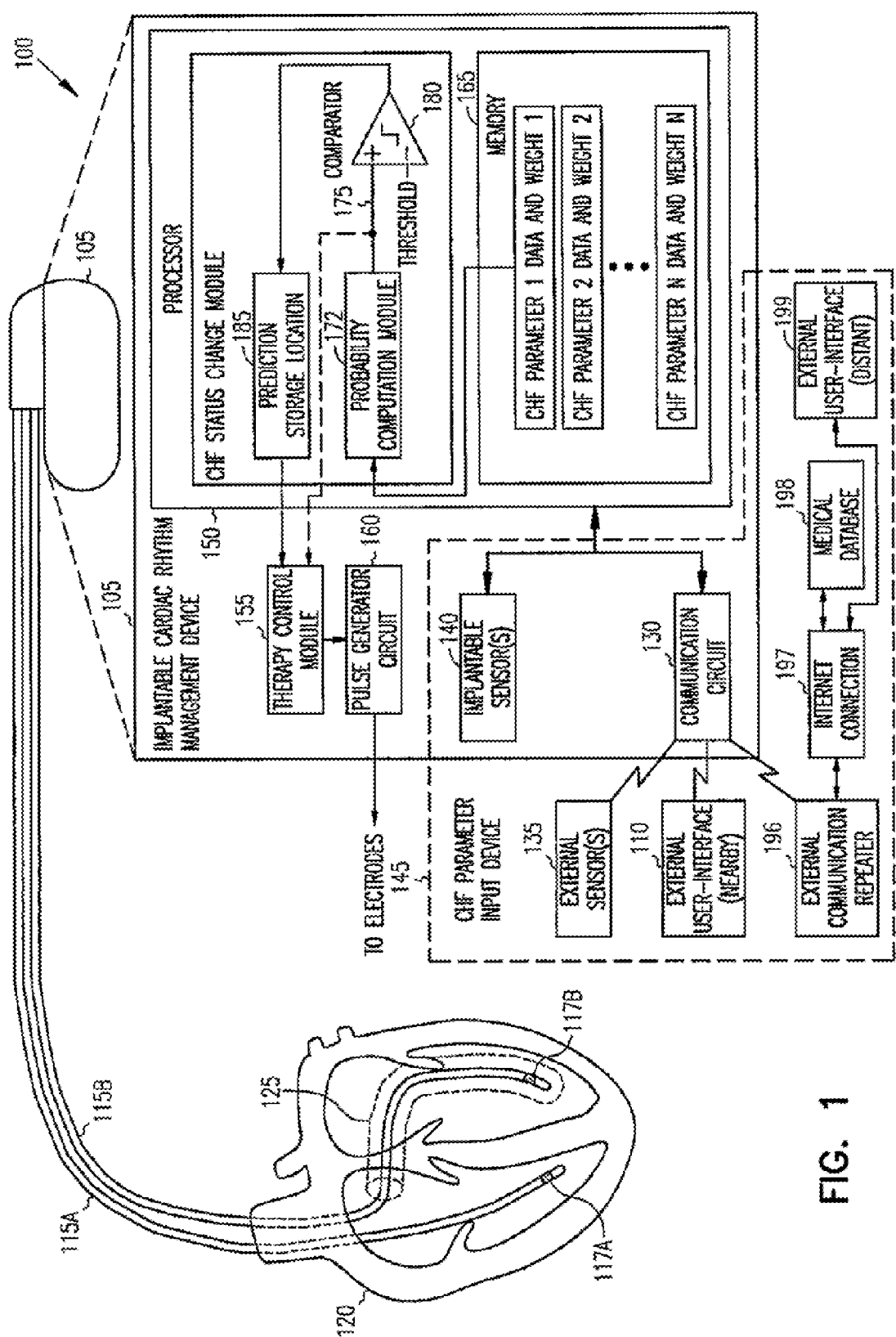

FIG. 2 is a graph illustrating generally, by way of example, but not by way of limitation, various CHF physiological parameters 200A–S, at least two of which are used in the probability computation 205 to provide a weighted probability at 210 of a CHF status change occurring during a predetermined future time period. The probability at 210 is computed by normalizing an indication of each of the two or more CHF physiological parameters 200A–S (to obtain $P_i$) and scaling each such normalized CHF physiological parameter 200A–S by its corresponding weight, $W_i$, and summing the resulting products.

In one example, fluid in the subject's lungs (i.e., acute pulmonary edema) is used as a CHF physiologic parameter 200A. In one example, acute pulmonary edema is measured by an implantable sensor 140 that senses transthoracic impedance, a low frequency component of which changes with edema status. In another example, acute pulmonary edema is measured on an X-ray by a user, and an indication of the degree of edema is input to CHF parameter input device 145 by the user at external user interface 110. An increase in pulmonary edema correlates to a future worsening of the subject's CHF status during the predetermined future time period.

In another example, the subject's weight is used as a CHF physiologic parameter 200B. In one example, the subject's weight is measured by an external sensor 135 having a scale coupled to a wireless communication circuit that is capable of communicating with communication circuit 130 in implantable device 105. In another example, the subject's weight is measured on an external scale, and manually input by the subject, caregiver, or another user to nearby external user interface 110, and wirelessly communicated to communication circuit 130 of implantable device 105. An increase in weight correlates to a future worsening of the subject's CHF status during the predetermined future time period.

In another example, the subject's shortness of breath while sleeping (i.e., paroxysmal nocturnal dyspnea) is used as a CHF physiologic parameter 200C. In one example, paroxysmal nocturnal dyspnea is measured by implantable sensors 140 including a respiration sensor (e.g., an impedance sensor) to detect the shortness of breath and a sleep detector. One example of a sleep detector is described in Carlson et al. U.S. patent application Ser. No. 09/802,316, entitled "CARDIAC RHYTHM MANAGEMENT SYSTEM USING TIME-DOMAIN HEART RATE VARIABILITY INDICIA," which is assigned to Cardiac Pacemakers, inc., and which is incorporated herein by reference in its entirety, including its description of a sleep detector. In another example, the subject, caregiver, or another user enters an indication of the degree of paroxysmal nocturnal dyspnea into nearby external user interface 110 of CHF parameter input device 145. An increase in paroxysmal nocturnal dyspnea correlates to a future worsening of the subject's CHF status during the predetermined future time period.

In another example, the subject's shortness of breath while lying down, i.e., orthopnea, is used as a CHF physiologic parameter 200D. In one example, orthopnea is measured by implantable sensors 140 including a respiration sensor (e.g., an impedance sensor) to detect the shortness of breath and a posture sensor (e.g., an accelerometer). In another example, the subject, caregiver, or another user enters an indication of the degree of orthopnea into external user interface 110 of CHF parameter input device 145. An increase in orthopnea correlates to a future worsening of the subject's CHF status during the predetermined future time period.

In another example, the subject's changed respiration sounds (e.g., increased rales) is used as a CHF physiologic parameter 200E. In one example, the changed respiration sounds are measured by implantable sensor 140 including a microphone, accelerometer, or other like sound detector. In another example, the subject, caregiver, or another user enters an indication of the degree of increased rales into external user interface 110 of CHF parameter input device 145. An increase in rales correlates to a future worsening of the subject's CHF status during the predetermined future time period.

In another example, the subject's heart sounds (for example, heart sounds referred to in the art as $S_1$, $S_2$, and particularly the heart sound referred to in the art as $S_3$) are used as a CHF physiologic parameter 200F. In one example, the heart sounds are measured by implantable accelerometer or other sensor 140, such as by using the systems and methods described in Lincoln et al. U.S. patent application Ser. No. 09/862,763, entitled "CARDIAC RHYTHM MANAGEMENT SYSTEM SELECTING A-V DELAY BASED ON INTERVAL BETWEEN ATRIAL DEPOLARIZATION AND MITRAL VALVE CLOSURE," and/or the systems and methods described in Lincoln et al. U.S. patent application Ser. No. 10/099,865, entitled "CARDIAC RHYTHM MANAGEMENT SYSTEM AND METHOD USING TIME BETWEEN MITRAL VALVE CLOSURE AND AORTIC EJECTION," each of which is assigned to Cardiac Pacemakers, Inc., and the disclosure of each of which is incorporated herein by reference in its entirety, including its description of heart sound detection. An increase in certain heart sounds (e.g., $S_3$) correlates to a future worsening of the subject's CHF status during the predetermined future time period.

In another example, the subject's neck vein distension (e.g., bulging neck vein) is used as a CHF physiologic parameter 200G. In one example, the subject, caregiver, or another user enters an indication of the degree of neck vein distension into external user interface 110 of CHF parameter input device 145. An increase in neck vein distension correlates to a future worsening of the subject's CHF status during the predetermined future time period.

In another example, the subject's abdominojugular reflex (e.g., bulging of neck vein upon applying compression to the subject's thorax) is used as a CHF physiologic parameter 200H. In one example, the subject, caregiver, or other user enters an indication of the degree of abdominojugular reflex into external user interface 110 of CHF parameter input device 145. An increase in abdominojugular reflex correlates to a future worsening of the subject's CHF status during the predetermined time period.

In another example, the subject's cardiomegaly (i.e., enlargement of heart) is used as a CHF physiologic parameter 200I. In one example, the subject's heart size is measured by implantable sensor 140 (e.g., a transthoracic impedance sensor). For example, a reduced cardiac stroke component of a transthoracic impedance signal correlates to an increase in heart size. In another example, the subject, caregiver, or another user enters an indication of the subject's heart size, based on an echocardiogram or other imaging measurement, into external user interface 110 of CHF parameter input device 145. An increase in heart size correlates to a future worsening of the subject's CHF status during the predetermined future time period.

In another example, the subject's intravascular blood pressure is used as a CHF physiologic parameter 200J. In one example, the subject's intravascular blood pressure is measured by implantable sensor 140 (e.g., a vena cava or right atrial pressure transducer). In another example, the subject, caregiver, or another user enters an indication of the subject's intravascular blood pressure (e.g., based on an external measurement) into external user interface 110 of CHF parameter input device 145. An increase in intravascular blood pressure correlates to a future worsening of the subject's CHF status during the predetermined future time period.

In another example, the subject's dyspnea on exertion is used as a CHF physiologic parameter 200K. In one example, the rapid shallow breathing associated with dyspnea is measured by implantable sensors 140 including a respiration sensor (e.g., an impedance sensor) and an activity sensor (e.g., an accelerometer) to detect exertion. For example, an increase in respiratory rate together with an increase in activity, if accompanied by a decrease in tidal volume of the respiration, is indicative of dyspnea on exertion. In another example, the subject, caregiver, or another user enters an indication of the subject's dyspnea on exertion into external user interface 110 of CHF parameter input device 145. An increase in dyspnea on exertion correlates to a future worsening of the subject's CHF status during the future predetermined time period.

In another example, the subject's night cough (or cough while lying down) is used as a CHF physiologic parameter 200L. In one example, the night cough is measured by an implantable sensor(s) 140 (e.g., a transthoracic impedance sensor) to detect the cough and a clock, a sleep detector, or a posture detector to respectively detect a time period during the night, the subject's sleep, and/or the subject's lying down. In another example, the subject, caregiver, or another user enters an indication of the subject's night cough into external user interface 110 of CHF parameter input device 145. An increase in night cough (or cough while lying down) correlates to a future worsening of the subject's CHF status during the future predetermined time period.

In another example, the subject's heart rate is used as a CHF physiologic parameter 200M. In one example, heart rate is measured using an implantable sensor 140 (e.g., a cardiac signal sense amplifier coupled to an electrode 117A and/or 117B). In another example, the subject, caregiver, or another user enters an indication of the subject's heart rate (e.g., based on an external measurement) into external user interface 110 of CHF parameter input device 145. An increase in heart rate (e.g., average resting heart rate) correlates to a future worsening of the subject's CHF status during the future predetermined time period.

In another example, the subject's pleural effusion (i.e., fluid in the subject's chest, but outside the subject's lungs) is used as a CHF physiologic parameter 200N. In one example, pleural effusion is measured by an implantable sensor 140 that senses transthoracic impedance, a low frequency component of which changes with pleural effusion status. In another example, pleural effusion is measured on an X-ray or other image by a user, and an indication of the degree of pleural effusion is input to CHF parameter input device 145 by the user at external user interface 110. An increase in pleural effusion correlates to a future worsening of the subject's CHF status during the predetermined future time period.

In another example, the subject's hepatomegaly (i.e., liver enlargement) is used as a CHF physiologic parameter 200O. In one example, hepatomegaly is measured on an X-ray or other image by a user, and an indication of the degree of hepatomegaly is input to CHF parameter input device 145 by the user at external user interface 110. An increase in hepatomegaly correlates to a future worsening of the subject's CHF status during the predetermined future time period.

In another example, the subject's peripheral edema (i.e., fluid retention in the extremities) is used as a CHF physiologic parameter 200P. In one example, a user, physician, or caregiver measures a swollen arm or leg (e.g., using a tape measure) and inputs an indication of the degree of peripheral edema to CHF parameter input device 145 at external user interface 110. An increase in peripheral edema correlates to a future worsening of the subject's CHF status during the predetermined future time period.

In another example, the subject's left ventricular end diastolic pressure (LVEDP) is used as CHF physiologic parameter 200Q. In one example, LVEDP is measured using an implantable pressure sensor 140 disposed within in the subject's left ventricle. An increase in LVEDP correlates to a future worsening of the subject's CHF status during the predetermined future time period.

In another example, the subject's left atrial pressure ("LA pressure") is used as CHF physiologic parameter 200R. In one example, LA pressure is measured using an implantable pressure sensor 140 disposed within in the subject's left atrium. An increase in LA pressure correlates to a future worsening of the subject's CHF status during the predetermined future time period.

In another example, the subject's brain natriaetic peptide (BNP) level is used as CHF physiologic parameter 200S. BNP is released by the subject's body in response to left ventricular stress. An increase in BNP correlates to a future worsening of the subject's CHF status during the predetermined future time period. In one example, the subject's BNP level is measured by an external blood test, and an indication of the BNP level is input to CHF parameter input device 145 by the user at external user interface 110. In another example, the subject's BNP level is measured by an implantable sensor 140 or an external (e.g., transdermal) sensor 135.

In a further example, therapy control module 155 adjusts a therapy being provided by pulse generator 160 to heart 120 based on at least one of the binary indication predicting whether a significant change in CHF status is expected to occur within a predetermined future time period or on the multivalued underlying probability of the change in CHF status. In one example, such therapy adjustment includes changing which electrodes are being used to deliver cardiac resynchronization therapy for spatially coordinating heart contractions.

In another example, such therapy adjustment includes initiating or adjusting paired pacing. Paired pacing involves delivering a premature electrical energy pulse to a portion of the heart during a time period that excites heart tissue, but does not cause a corresponding heart contraction. The energy thus delivered increases an intracellular calcium concentration, and is followed by delivery of a second energy pulse during an immediately subsequent time period that does trigger a resulting heart contraction. Thus, in this example, pacing a particular heart chamber of a subject at 75 beats per minute includes delivering pairs of pacing pulses at the 75 beats per minute rate, the first pacing pulse in the pair increasing intracellular calcium concentration, but not triggering a resulting heart chamber contraction, and the second pacing pulse in the pair using the increased calcium concentration in triggering a resulting heart chamber contraction.

In an alternative example, the probability computation 205 takes the form of a conditional probability computation, such as described in Sweeney et al. U.S. Pat. No. 6,272,377, which is assigned to Cardiac Pacemakers, Inc., and which is incorporated by reference herein in its entirety, including its description of using conditional probabilities to predict the likelihood of occurrence of a future event. In the present context, the future event is a CHF status change, and the CHF physiologic parameters serve as triggers/markers or, more generally, conditioning events. The weights correlating each CHF physiologic parameter to a future CHF status change are conditional probabilities that may alternatively be expressed as rates, as described in the above-incorporated Sweeney et al. reference.

One such example includes detecting a conditioning event (e.g., one of CHF physiologic parameters 200A–S) statistically associated with the occurrence of a CHF status change in a subject. In this example, device 105 predicts the occurrence of a CHF status change within a specified prediction time period if an estimated CHF status change probability exceeds a specified threshold value. The estimated CHF status change probability is computed from a conditional CHF status change probability, associated with the conditioning event, that is derived from past observations of instances in which the conditioning event occurs alone or together with a CHF status change within a specified time period.

In a further example, the conditional CHF status change probability CP is a ratio of the number of observed instances in which the conditioning event is followed by a CHF status change within a specified basic time period to the total number of observed instances of the conditioning event. In a further example, this involves estimating a rate C at which the conditioning event occurs. The estimated CHF status change probability is then calculated by the expression:

$$\text{estimated } CHF \text{ status change probability} = CP \times (1 - e^{-CT}),$$

where T is a measure of the specified prediction time period. In one example, the conditional CHF status change probability is calculated by the expression:

$$CP = 1 - e^{-RT},$$

where T is a measure of the specified prediction time period, and R is an estimate of the rate at which the CHF status changes occur while the conditioning event is present. In a further example, a plurality of conditioning events statistically associated with the occurrence of a CHF status change are detected, and a composite estimated CHF status change probability is compared with a threshold value in order to predict the occurrence of a CHF status change. The composite CHF status change probability is associated with a combination of the estimated CHF status change probabilities associated with each detected conditioning event, such as described in the above-incorporated Sweeney et al. reference.

It is to be understood that the above description is intended to be illustrative, and not restrictive. For example, the above-discussed examples may be used in combination with each other. Many other embodiments will be apparent to those of skill in the art upon reviewing the above description. The scope of the invention should, therefore, be determined with reference to the appended claims, along with the full scope of equivalents to which such claims are entitled. Moreover, the terms "first," "second," "third," etc. are used merely as labels, and are not intended to impose numeric requirements on their objects.

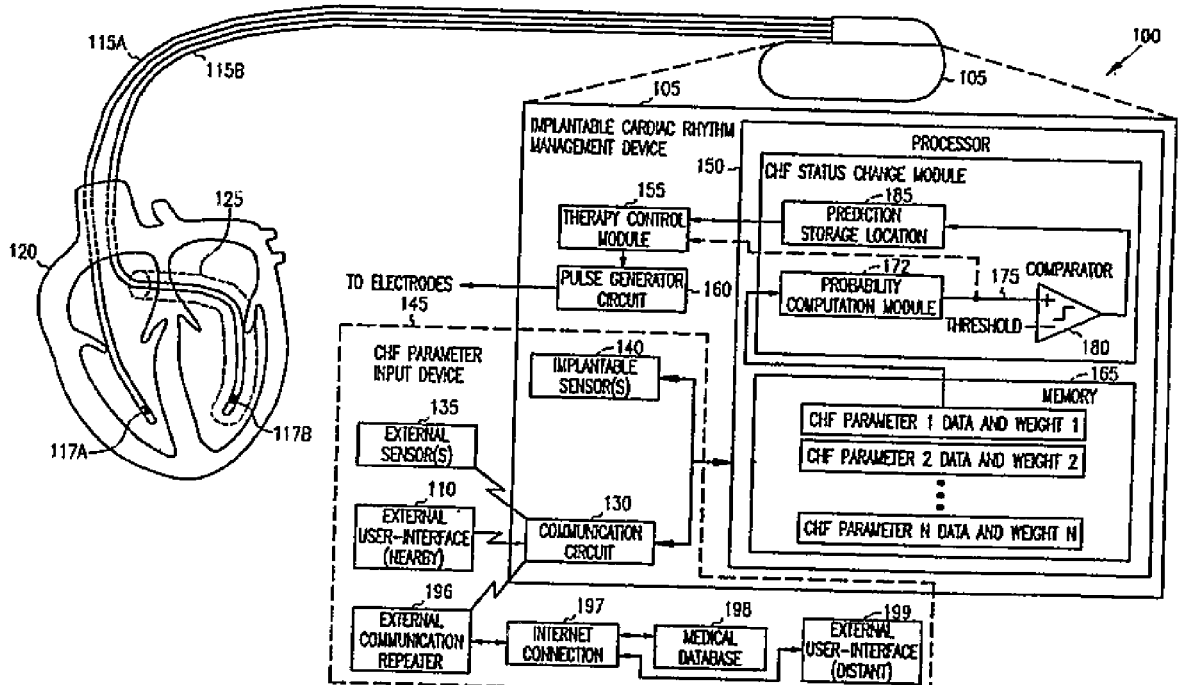

What is claimed is:

1. A cardiac rhythm management system comprising:
   an implantable cardiac rhythm management device comprising:
      at least one congestive heart failure (CHF) physiologic parameter input device to provide CHF physiologic information about a subject, the CHF physiologic information comprising information about at least one of the subject's dyspnea, orthopnea, neck vein distension, abdominojugular reflex, cough, hepatomegaly, peripheral edema, brain patriaretic peptide (BNP) level, or at least one of pulmonary edema, cardiomegaly, or pleural effusion wherein the input device comprises an implantable transthoracic impedance sensor configured to provide information about the subject's pulmonary edema, cardiomegaly, or pleural effusion; and
      a processor circuit, comprising at least one processor input coupled to the at least one CHF physiologic parameter input device to receive a plurality of different CHF physiologic parameters, the processor comprising:
         weighting factors, stored in a memory, the weighting factors corresponding to each of the received CHF physiologic parameters; and
         a CHF status change probability indicator, to predict a likelihood of a subsequent change in a CHF status of a subject using the plurality of different received CHF physiologic parameters and corresponding weighting factors; and
   an external remote user interface communicatively couplable to the implantable cardiac rhythm management device, the external remote user interface comprising a user-detectable indication of the CHF status change probability indicator received from the implantable cardiac rhythm management device, in which the remote user interface comprises a user input device to receive at least one CHF physiologic parameter from a user and to communicate to the at least one CHF physiological parameter input device in the implantable cardiac rhythm management device the at least one CHF physiological parameter selected from the group consisting of at least one or more of the subject's dyspnea, orthopnea, neck vein distension, abdominojugular reflex, cough, hepatomegaly, peripheral edema, brain natriaretic peptide (BNP) level, pulmonary edema, cardiomegaly, or pleural effusion.

2. The system of claim 1, in which a first weighting parameter corresponding to a first received CHF physiologic parameter, used to predict the likelihood of a subsequent change in the CHF status of the subject, depends on which at least one other received CHF physiologic parameter is also used to predict the likelihood of a subsequent change in CHF status.

3. The system of claim 1, in which a first weighting parameter corresponding to a first received CHF physiologic parameter, used to predict the likelihood of a subsequent change in the CHF status of the subject, depends on the number of other received CHF physiologic parameters that are also used to predict the likelihood of a subsequent change in CHF status.

4. The system of claim 1, in which the CHF status change probability indicator, is configured to predict a likelihood of a subsequent change in a CHF status of a subject by comparing to a threshold value a probability computed using the plurality of different received CHF physiologic parameters and corresponding weighting factors.

5. The system of claim 1, in which at least one of the weighting factors is computed using historical data relating its corresponding CHF physiologic parameter to CHF status.

6. The system of claim 5, in which the historical data is obtained from the same subject from which the CHF physiologic information is obtained.

7. The system of claim 5, in which the historical data is obtained from at least one subject other than the subject from which the CHF physiologic information is obtained.

8. The system of claim 1, further comprising a therapy control module configured to adjust a therapy provided to the subject using at least the CHF status change probability indicator.

9. The system of claim 1, in which the user interface is configured to receive from the user at least one CHF physiologic parameter further comprising information about the subject's weight to communicate to the at least one CHF physiologic parameter input device in the implantable cardiac rhythm management device.

10. The system of claim 9, in which the user interface is configured to receive from the user at least one CHF physiologic parameter comprising information about the subject's dyspnea to communicate to the at least one CHF physiologic parameter input device in the implantable cardiac rhythm management device.

11. The system of claim 9, in which the user interface is configured to receive from the user at least one CHF physiologic parameter comprising information about the subject's orthopnea to communicate to the at least one CHF physiologic parameter input device in the implantable cardiac rhythm management device.

12. The system of claim 9, in which the user interface is configured to receive from the user at least one CHF physiologic parameter comprising information about the subject's neck vein distension to communicate to the at least one CHF physiologic parameter input device in the implantable cardiac rhythm management device.

13. The system of claim 9, in which the user interface is configured to receive from the user at least one CHF physiologic parameter comprising information about the subject's abdominojugular reflex to communicate to the at least one CHF physiologic parameter input device in the implantable cardiac rhythm management device.

14. The system of claim 9, in which the user interface is configured to receive from the user at least one CHF physiologic parameter comprising information about the subject's cough to communicate to the at least one CHF physiologic parameter input device in the implantable cardiac rhythm management device.

15. The system of claim 9, in which the user interface is configured to receive from the user at least one CHF physiologic parameter comprising information about the subject's hepatomegaly to communicate to the at least one CHF physiologic parameter input device in the implantable cardiac rhythm management device.

16. The system of claim 9, in which the user interface is configured to receive from the user at least one CHF physiologic parameter comprising information about the subject's peripheral edema to communicate to the at least one CHF physiologic parameter input device in the implantable cardiac rhythm management device.

17. The system of claim 9, in which the user interface is configured to receive from the user at least one CHF physiologic parameter comprising information about the subject's brain natriaretic peptide (BNP) level.

18. The system of claim 1, in which the at least one congestive heart failure (CHF) physiologic parameter input device of the implantable cardiac rhythm management device comprises an implantable transthoracic impedance sensor configured to provide information about the subject's pulmonary edema.

19. The system of claim 1, in which the at least one congestive heart failure (CHF) physiologic parameter input device of the implantable cardiac rhythm management device comprises an implantable transthoracic impedance sensor configured to provide information about the subject's cardiomegaly.

20. The system of claim 1, in which the at least one congestive heart failure (CHF) physiologic parameter input device of the implantable cardiac rhythm management device comprises an implantable transthoracic impedance sensor configured to provide information about the subject's pleural effusion.

21. The system of claim 1, in which the at least one congestive heart failure (CHF) physiologic parameter input device of the implantable cardiac rhythm management device comprises implantable respiration and posture sensors configured to provide information about the subject's dyspnea.

22. The system of claim 1, in which the at least one congestive heart failure (CHF) physiologic parameter input device of the implantable cardiac rhythm management device comprises an implantable sound sensor configured to provide information about the subject's respiration sounds.

23. The system of claim 1, in which the at least one congestive heart failure (CHF) physiologic parameter input device of the implantable cardiac rhythm management device comprises an implantable sound sensor configured to provide information about the subject's heart contraction sounds.

24. The system of claim 1, in which the at least one congestive heart failure (CHF) physiologic parameter input device of the implantable cardiac rhythm management device comprises an implantable pressure sensor configured to provide information about the subject's intravascular pressure.

25. The system of claim 1, in which the at least one congestive heart failure (CHF) physiologic parameter input device of the implantable cardiac rhythm management device comprises pressure sensor sized and shaped to be placed in at least one of a left ventricle and a left atrium for providing an intracardiac pressure measurement, the intracardiac pressure measurement comprising at least one of a left ventricular end diastolic pressure (LVEDP) measurement and a left atrial (LA) pressure measurement.

26. The system of claim 1, further comprising an external scale communicatively couplable to the implantable cardiac rhythm management device, the scale configured to communicate information about the subject's weight to the at least one congestive heart failure (CHF) physiologic parameter input device of the implantable cardiac rhythm management device.

27. A cardiac rhythm management system comprising:
an implantable cardiac rhythm management device comprising:
means for providing at least one congestive heart failure (CHF) physiologic parameter about a subject, the CHF physiologic information comprising information about at least one of the subject's dyspnea, orthopnea, neck vein distension, abdominojugular reflex, cough, hepatomegaly, peripheral edema, brain natriaretic peptide (BNP) level, pulmonary edema, cardiomegaly, or pleural effusion; and a processor circuit, comprising at least one processor input coupled to the at least one CHF physiologic parameter input device to receive a plurality of different CHF physiologic parameters, the processor comprising:
weighting factors, stored in a memory, the weighting factors corresponding to each of the received CHF physiologic parameters; and
a CHF status change probability indicator, to predict a likelihood of a subsequent change in a CHF status of a subject using a probability computed using the plurality of different received CHF physiologic parameters and corresponding weighting factors; and
an external remote user interface communicatively couplable to the implantable cardiac rhythm management device, the external remote user interface comprising a user-detectable indication of the CHF status change probability indicator received from the implantable cardiac rhythm management device, in which the remote user interface comprises a user input device to receive at least one CHF physiologic parameter from a user and to communicate to the at least one CHF physiological parameter input device in the implantable cardiac rhythm management device the at least one CHF physiological parameter selected from the group consisting of at least one or more of the subject's dyspnea, orthopnea, neck vein distension, abdominojugular reflex, cough, hepatomegaly, peripheral edema, brain natriaretic peptide (BNP) level, pulmonary edema, cardiomegaly, or pleural effusion.

28. A cardiac rhythm management system comprising:
an implantable cardiac rhythm management device comprising:
at least one congestive heart failure (CHF) conditioning event input device to provide a CHF conditioning event statistically associated with the occurrence of a CHF status change in a subject;
a processor circuit, comprising at least one processor input coupled to the at least one CHF conditioning event input device to receive the CHF conditioning event, the processor comprising an indicator predicting the occurrence of a CHF status change within a specified prediction time period if an estimated CHF status change probability exceeds a specified threshold value, wherein the estimated CHF status change probability is computed from a conditional CHF status change probability, associated with the conditioning event, that is derived from past observations of instances in which the conditioning event occurs alone or together with a CHF status change within a specified time period; and
wherein the processor is adapted to estimate a rate C at which the conditioning event occurs, and further wherein the estimated CHF status change probability is calculated by the expression: estimated CHF status change probability=$CP \times (1-e^{-CT})$.

29. The system of claim 28, in which the conditional CHF status change probability is a ratio of the number of observed instances in which the conditioning event is followed by a CHF status change within a specified basic time period to the total number of observed instances of the conditioning event.

30. The system of claim 28, wherein the conditional CHF status change probability is calculated by the expression:

$$CP = 1 - e^{-RT},$$

wherein T is a measure of the specified prediction time period, and R is an estimate of the rate at which CHF status changes occur while the conditioning event is present.

31. A method comprising:
obtaining a plurality of different congestive heart failure (CHF) physiologic parameters about a subject for predicting a CHF status change, in which the obtaining the plurality of different CHF physiologic parameters about the subject comprises at least one of:
receiving a user input information about at least one of the subject's dyspnea, orthopnea, neck vein distention, abdominojugular reflex, cough, hepatomegaly, peripheral edema, and brain natiaretic peptide (BNP) level; and sensing a thoracic impedance to obtain information about at least one of the subject's pulmonary edema, cardiomegaly, and pleural effusion;
weighting each of the CHF physiologic parameters to provide corresponding weighted CHF physiologic parameters;
computing a CHF status change probability using the weighted CHF physiologic parameters; and
using the computed CHF status change probability in predicting whether the subject's CHF status will undergo a significant change within a specified subsequent time period.

32. The system of claim 31, in which the weighting each of the CHF physiologic parameters comprises weighting a first CHF physiologic parameter depending at least in part on which other CHF physiologic parameters are obtained from the patient for predicting the CHF status change.

33. The system of claim 31, in which the weighting each of the CHF physiologic parameters comprises weighting a first CHF physiologic parameter depending at least in part on how many other CHF physiologic parameters are obtained from the patient for predicting the CHF status change.

34. The method of claim 31, in which the predicting whether the subject's CHF status will undergo a significant change within a specified time period comprises comparing the computed CHF status change probability to a threshold.

35. The method of claim 31, further comprising adjusting a therapy provided by an implantable cardiac rhythm management device to the subject using at least the computed CHF status change probability.

36. The method of claim 31, in which the weighting comprises weighting at least one of the CHF physiologic parameters using historical data obtained from the subject.

37. The method of claim 31, in which the weighting comprises weighting at least one of the CHF physiologic parameters using historical data obtained from a different subject.

38. The method of claim 31, in which the obtaining the plurality of different CHF physiologic parameters about the subject comprises receiving a user input including information about the subject's weight.

39. The method of claim 31, in which the obtaining the plurality of different CHF physiologic parameters about the subject comprises receiving a user input including information about the subject's dyspnea.

40. The method of claim 31, in which the obtaining the plurality of different CHF physiologic parameters about the subject comprises receiving a user input including information about the subject's orthopnea.

41. The method of claim 31, in which the obtaining the plurality of different CHF physiologic parameters about the subject comprises receiving a user input including information about the subject's neck vein distention.

42. The method of claim 31, in which the obtaining the plurality of different CHF physiologic parameters about the subject comprises receiving a user input including information about the subject's abdominojugular reflex.

43. The method of claim 31, in which the obtaining the plurality of different CHF physiologic parameters about the subject comprises receiving a user input including information about the subject's cough.

44. The method of claim 31, in which the obtaining the plurality of different CHF physiologic parameters about the subject comprises receiving a user input including information about the subject's hepatomegaly.

45. The method of claim 31, in which the obtaining the plurality of different CHF physiologic parameters about the subject comprises receiving a user input including information about the subject's peripheral edema.

46. The method of claim 31, in which the obtaining the plurality of different CHF physiologic parameters about the subject comprises receiving a user input including information about the subject's brain natiaretic peptide (BNP) level.

47. The method of claim 31, in which the obtaining the plurality of different CHF physiologic parameters about the subject comprises sensing a transthoracic impedance to obtain information about the subject's pulmonary edema.

48. The method of claim 31, in which the obtaining the plurality of different CHF physiologic parameters about the subject comprises sensing a transthoracic impedance to obtain information about the subject's cardiomegaly.

49. The method of claim 31, in which the obtaining the plurality of different CHF physiologic parameters about the subject comprises sensing a transthoracic impedance to obtain information about the subject's pleural effusion.

50. The method of claim 31, in which the obtaining the plurality of different CHF physiologic parameters about the subject comprises sensing respiration and posture to obtain information about the subject's dyspnea.

51. The method of claim 31, in which the obtaining the plurality of different CHF physiologic parameters about the subject comprises sensing the subject's respiration sounds.

52. The method of claim 31, in which the obtaining the plurality of different CHF physiologic parameters about the subject comprises sensing the subject's heart contraction sounds.

53. The method of claim 31, in which the obtaining the plurality of different CHF physiologic parameters about the subject comprises sensing the subject's intravascular pressure.

54. The method of claim 31, in which the obtaining the plurality of different CHF physiologic parameters about the subject comprises sensing the subject's intracardiac pressure selected from the group consisting of a left ventricular end-diastolic pressure (LVEDP) and a left atrial (LA) pressure.

55. The method of claim 31, in which the obtaining the plurality of different CHF physiologic parameters about the subject comprises measuring the subject's weight at an external scale and telemetering the subject's weight from the external scale to an implantable cardiac rhythm management device.

* * * * *

UNITED STATES PATENT AND TRADEMARK OFFICE
CERTIFICATE OF CORRECTION

PATENT NO. : 7,127,290 B2
APPLICATION NO. : 10/213268
DATED : October 24, 2006
INVENTOR(S) : Girouard et al.

It is certified that error appears in the above-identified patent and that said Letters Patent is hereby corrected as shown below:

Title page on sheet 1 of 2, in FIG. 1 (Box 172), line 1, delete "PROBABILTY" and insert -- PROBABILITY --, as therefore attached on the attached page.

In column 11, line 11, in Claim 1, delete "patriaretic" and insert -- natriaretic --, therefor.

In column 11, line 46, in Claim 1, delete "natriaretic" and insert -- natriuretic --, therefor.

In column 12, line 65, in Claim 17, delete "natriaretic" and insert -- natriuretic --, therefor.

In column 13, line 66, in Claim 27, delete "natriaretic" and insert -- natriuretic --, therefor.

In column 14, line 30, in Claim 27, delete "natriaretic" and insert -- natriuretic --, therefor.

In column 14, line 38, in Claim 28, after "subject;" insert -- and --.

In column 15, line 14, in Claim 31, delete "natiaretic" and insert -- natriuretic --, therefor.

In column 16, line 23, in Claim 46, delete "natiaretic" and insert -- natriuretic --, therefor.

Signed and Sealed this

Eleventh Day of December, 2007

JON W. DUDAS
*Director of the United States Patent and Trademark Office*

(12) United States Patent
Girouard et al.

(10) Patent No.: US 7,127,290 B2
(45) Date of Patent: Oct. 24, 2006

(54) CARDIAC RHYTHM MANAGEMENT SYSTEMS AND METHODS PREDICTING CONGESTIVE HEART FAILURE STATUS

(75) Inventors: Steven D. Girouard, Woodbury, MN (US); Jeffrey E. Stahmann, Ramsey, MN (US); Robert J. Sweeney, Woodbury, MN (US); Bruce H. KenKnight, Maple Grove, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 610 days.

(21) Appl. No.: 10/213,268

(22) Filed: Aug. 6, 2002

(65) Prior Publication Data
US 2003/0055461 A1 Mar. 20, 2003

Related U.S. Application Data

(63) Continuation-in-part of application No. 09/850,537, filed on May 7, 2001, now Pat. No. 7,050,846, which is a continuation of application No. 09/411,345, filed on Oct. 1, 1999, now Pat. No. 6,272,377.

(51) Int. Cl.
*A61N 1/365* (2006.01)
(52) U.S. Cl. .................................... 607/17; 600/515
(58) Field of Classification Search ............. 600/515; 607/17
See application file for complete search history.

(56) References Cited

U.S. PATENT DOCUMENTS

| | | | | |
|---|---|---|---|---|
| 4,129,125 A | * | 12/1978 | Lester et al. ............. 600/484 |
| 4,422,459 A | | 12/1983 | Simson ..................... 128/702 |
| 4,458,691 A | | 7/1984 | Netravali .................. 128/705 |
| 4,458,692 A | | 7/1984 | Simson ..................... 128/705 |
| 4,492,235 A | | 1/1985 | Sitrick ...................... 128/705 |
| 4,519,395 A | | 5/1985 | Hrushesky ............... 128/671 |
| 4,680,708 A | | 7/1987 | Ambos et al. ............ 364/417 |
| 4,732,157 A | | 3/1988 | Kaplan et al. ............ 128/696 |
| 4,754,753 A | | 7/1988 | King ......................... 128/699 |
| 4,777,960 A | | 10/1988 | Berger et al. ............. 128/706 |
| 4,905,706 A | | 3/1990 | Duff et al. ................ 128/701 |
| 4,924,875 A | | 5/1990 | Chamoun ................. 128/696 |
| 4,930,075 A | | 5/1990 | Kortas .................. 364/413.06 |
| 4,957,115 A | * | 9/1990 | Selker ........................ 600/509 |
| 4,960,129 A | | 10/1990 | dePaola et al. ........... 128/695 |
| 5,003,976 A | * | 4/1991 | Alt ............................ 607/18 |
| 5,014,698 A | | 5/1991 | Cohen ....................... 128/419 |
| 5,020,540 A | | 6/1991 | Chamoun ................. 128/696 |
| 5,042,497 A | | 8/1991 | Shapland .................. 128/696 |
| 5,092,341 A | | 3/1992 | Kelen ....................... 128/702 |

(Continued)

FOREIGN PATENT DOCUMENTS

EP 0547733 6/1993

(Continued)

OTHER PUBLICATIONS

Carlson, Gerrard.M., et al., "Cardiac Rhythm Management System Using Time-Domain Heart Rate Variability Indicia", U.S. Appl. No. 09/802,316, (Mar. 8, 2001), 34.

(Continued)

*Primary Examiner*—Angela D. Sykes
*Assistant Examiner*—Lenwood Faulcon, Jr.
(74) *Attorney, Agent, or Firm*—Schwegman, Lundberg, Woessner & Kluth, P.A.

(57) ABSTRACT

This document describes, among other things, systems, devices, and methods for predicting how the status of the patient's congestive heart failure (CHF) condition will progress in the future. In one example, a therapy is provided or adjusted at least in part in response to the prediction.

55 Claims, 2 Drawing Sheets